(12) United States Patent
Adaie (10) Patent No.: US 9,539,170 B1
(45) Date of Patent: Jan. 10, 2017

(54) LACRIMAL DUCT THERAPY DEVICE

(71) Applicant: Hamdah J. S. Adaie, Safat (KW)

(72) Inventor: Hamdah J. S. Adaie, Safat (KW)

( * ) Notice: Subject to any disclaimer, the term of this patent is extended or adjusted under 35 U.S.C. 154(b) by 0 days.

(21) Appl. No.: 15/243,744

(22) Filed: Aug. 22, 2016

(51) Int. Cl.
*A61H 23/00* (2006.01)
*A61H 5/00* (2006.01)

(52) U.S. Cl.
CPC ............... *A61H 23/006* (2013.01); *A61H 5/00* (2013.01); *A61H 23/004* (2013.01); *A61H 2201/0207* (2013.01); *A61H 2201/1604* (2013.01); *A61H 2201/1607* (2013.01); *A61H 2201/5097* (2013.01); *A61H 2205/023* (2013.01); *A61H 2205/024* (2013.01)

(58) Field of Classification Search
CPC ........ A61H 5/00; A61H 23/00; A61H 23/004; A61H 23/006; A61H 23/0254; A61H 23/0263; A61H 2023/002; A61H 2201/1604; A61H 2201/1607; A61H 2205/02; A61H 2205/022; A61H 2205/023; A61H 2205/024; A61H 2205/025; A61H 2205/027; A61H 2205/028; A61F 9/0008; A61F 9/0026; A61F 9/00772
USPC ......................................... 601/37, 67, 69, 70
See application file for complete search history.

(56) References Cited

U.S. PATENT DOCUMENTS

| | | | |
|---|---|---|---|
| 2,965,099 A | 12/1960 | Aufricht | |
| 4,573,982 A | 3/1986 | Forbes et al. | |
| 4,841,954 A * | 6/1989 | Kalsi | A61H 23/0263 601/71 |
| 4,920,466 A * | 4/1990 | Liu | A61H 23/0263 362/105 |
| 5,467,147 A | 11/1995 | Faranda | |
| 5,832,930 A | 11/1998 | Martin et al. | |
| 6,006,746 A * | 12/1999 | Karell | A61F 5/08 128/200.24 |
| 8,147,467 B2 | 4/2012 | Chen | |
| 2006/0012974 A1* | 1/2006 | Su | G02C 11/04 362/105 |
| 2011/0071481 A1* | 3/2011 | Chen | A61B 17/12 604/290 |
| 2011/0139163 A1* | 6/2011 | Hillila | A61H 23/00 128/861 |
| 2011/0313481 A1* | 12/2011 | De Vos | A61H 39/002 607/3 |

(Continued)

FOREIGN PATENT DOCUMENTS

CN 104586565 5/2015

*Primary Examiner* — Steven Douglas
*Assistant Examiner* — Kathrynn Lyddane
(74) *Attorney, Agent, or Firm* — Richard C. Litman (57) ABSTRACT

The lacrimal duct therapy device includes a frame assembly and an actuator assembly mounted on the frame assembly. The actuator assembly includes a contact assembly and a motor assembly configured to drive the contact assembly. The contact assembly includes at least one cam member having a base portion and a lobe portion and at least one arm member. The at least one cam member is mounted on a rod member attached to the motor assembly for rotation therewith. The at least one cam member bears against a leg member pivotally attached to the frame assembly, the leg member terminating in a knob bearing against the user's lacrimal duct region. Actuation of the motor periodically pivots the leg member so that the knob massages the lacrimal duct.

17 Claims, 7 Drawing Sheets

(56) References Cited

U.S. PATENT DOCUMENTS

| | | | |
|---|---|---|---|
| 2015/0289878 A1* | 10/2015 | Tal | A61H 7/001 606/204.25 |
| 2015/0343189 A1* | 12/2015 | Ostrovsky | A61N 1/0456 601/46 |

* cited by examiner

LACRIMAL DUCT THERAPY DEVICE

BACKGROUND OF THE INVENTION

1. Field of the Invention

The present invention relates to medical devices, and more particularly to a lacrimal duct therapy device for providing therapy to alleviate pain and/or pressure in the user's lacrimal duct.

2. Description of the Related Art

The lacrimal duct ("nasolacrimal duct") facilitates the movement of tears from a lacrimal sac into the nasal cavity. The opening of the nasolacrimal duct into the inferior nasal meatus is partially covered by a mucosal fold. Excess tears flow through the lacrimal duct, which drains into the inferior nasal meatus. The lacrimal duct is lined by stratified columnar epithelium containing mucus-secreting goblet cells and is surrounded by connective tissue.

Occasionally, a user may suffer blockage and/or pain in the lacrimal duct. Because the lacrimal duct is located above the nasal cavity, it can be difficult for the user to alleviate the blockage without forcing an evasive tool through the nose. Such a procedure may force the blockage further into the lacrimal duct, causing more pain or damage, instead of alleviating the pressure or blockage. Thus, a lacrimal duct therapy device solving the aforementioned problems is desired.

SUMMARY OF THE INVENTION

The lacrimal duct therapy device includes a frame assembly and an actuator assembly mounted on the frame assembly. The actuator assembly includes a contact assembly and a motor assembly configured for driving the contact assembly. The contact assembly includes at least one cam member having, a base portion and a lobe portion. The cam member is connected to the motor assembly via a rod member. The contact assembly also includes at least one arm member positioned in operative engagement with the at least one cam member. The arm member is configured to engage a region on the user's face to selectively provide therapeutic massaging pressure to the lacrimal duct. Activation of the motor assembly rotates the rod member connected to the at least one cam member. Rotation of the cam member engages the arm member so that the lobe portion of the cam member forces the arm member outward into a protracted position, thereby exerting a force on the user's face at the selected region. As the cam member continues to rotate, the base portion of the cam member allows the arm member to retract, disengaging the facial region.

The frame assembly may include a first arm member and a second arm member configured to attach the lacrimal duct therapy device to the user's ears and a bridge member positioned central to the first and second arm members and connected to the actuator assembly so that in a mounted position on the head of the user, the actuator assembly is positioned proximate to the user's nose.

The at least one arm member may have a planar first surface positioned in engagement with the at least one cam member and an opposing second surface having a knob member positioned to engage the surface of the user's face.

The contact assembly may include dual leg members provided at opposing ends of the rod member in aligned engagement with dual cam members so that rotational movement of the rod member rotates the dual cam members, forcing the dual leg members to pivot, providing a force on two regions of the user's face proximate to the lacrimal duct.

A biasing member may be connected to the leg member, providing a force that pulls the leg member inward, disengaging the arm member from the user's face.

The dual cam members, when so equipped, are configured in an alternating manner on the rod member so that rotation of the rod member by the motor forces the lobe portion of one of the cam members to force one of the arm members outward in an engaging protracted position to engage the user's face, while the other cam member engages a base portion of a respective cam member, positioning the respective arm member in a non-engaging retracted position.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
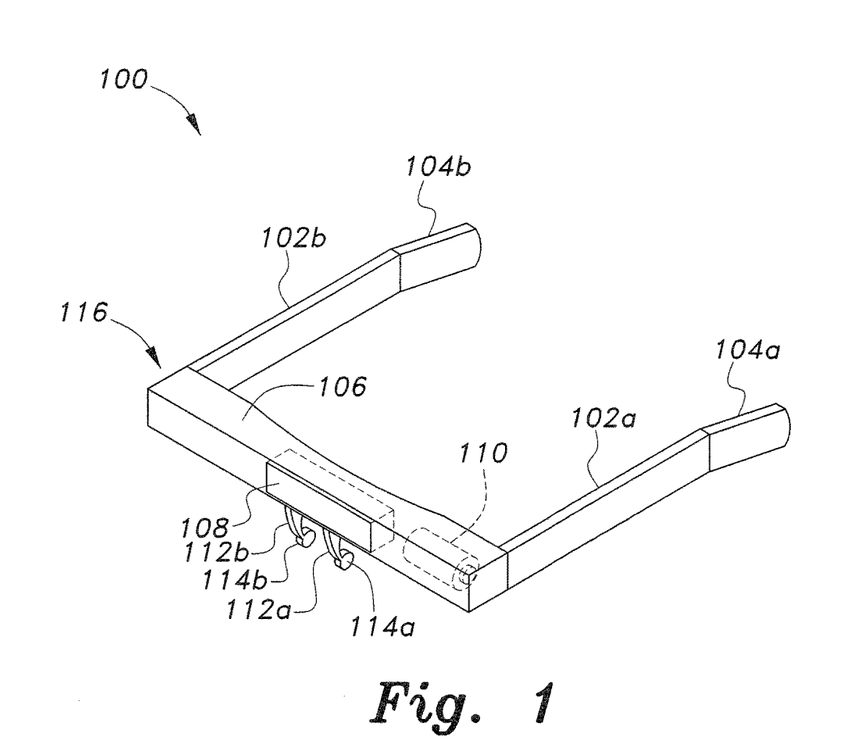
FIG. 1 is a top perspective view of a lacrimal duct therapy device according to the present invention.
Figure 3:
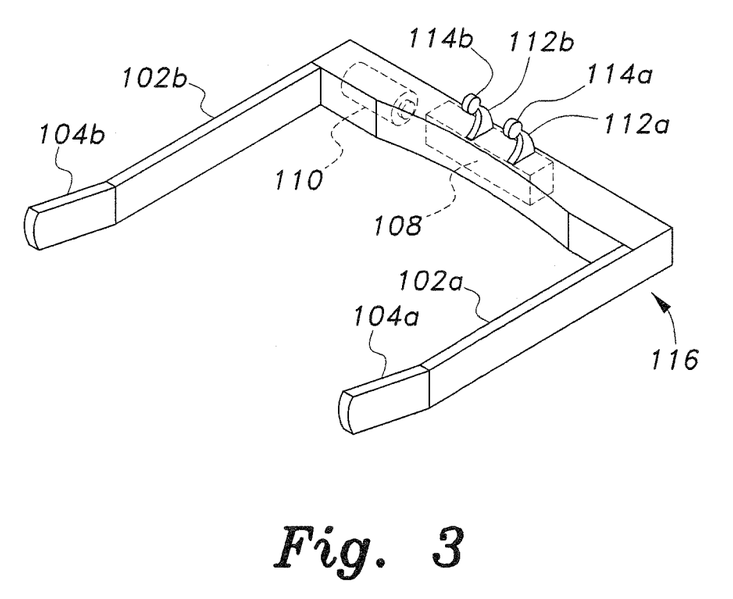
FIG. 3 is bottom perspective view of the lacrimal duct therapy device of FIG. 1.

The lacrimal duct therapy device is configured to provide therapeutic massaging pressure to an external region of a user's face proximate to the lacrimal duct. Referring to FIGS. 1 and 3, the lacrimal duct therapy device 100 includes a frame assembly 116 and an actuator assembly 108 for providing a massaging and/or vibrational therapy to the lacrimal duct.

The frame assembly 116 may have a conventional eyeglass frame configuration, including dual arm members or support members 102a, 102b configured to engage temporal regions on opposing sides of the user's head, thereby permitting the device 100 to be removably affixed to the user's head. The frame assembly 116 further includes a bridge member 106 extending between the respective support members 102a, 102b and configured for engagement with the user's forehead region. Each support member 102a, 102b includes a respective ear latch member 104a, 104b, which are adaptable for latching engagement with the user's ears.

The actuator assembly 108 is powered by a power source 110, which may be a rechargeable ion battery, for example. The bridge member 106 provides a cavity for containing and supporting a portion of the actuator assembly 108 therein. The bridge member 106 also provides a cavity for containing the power source 110.

Figure 4:
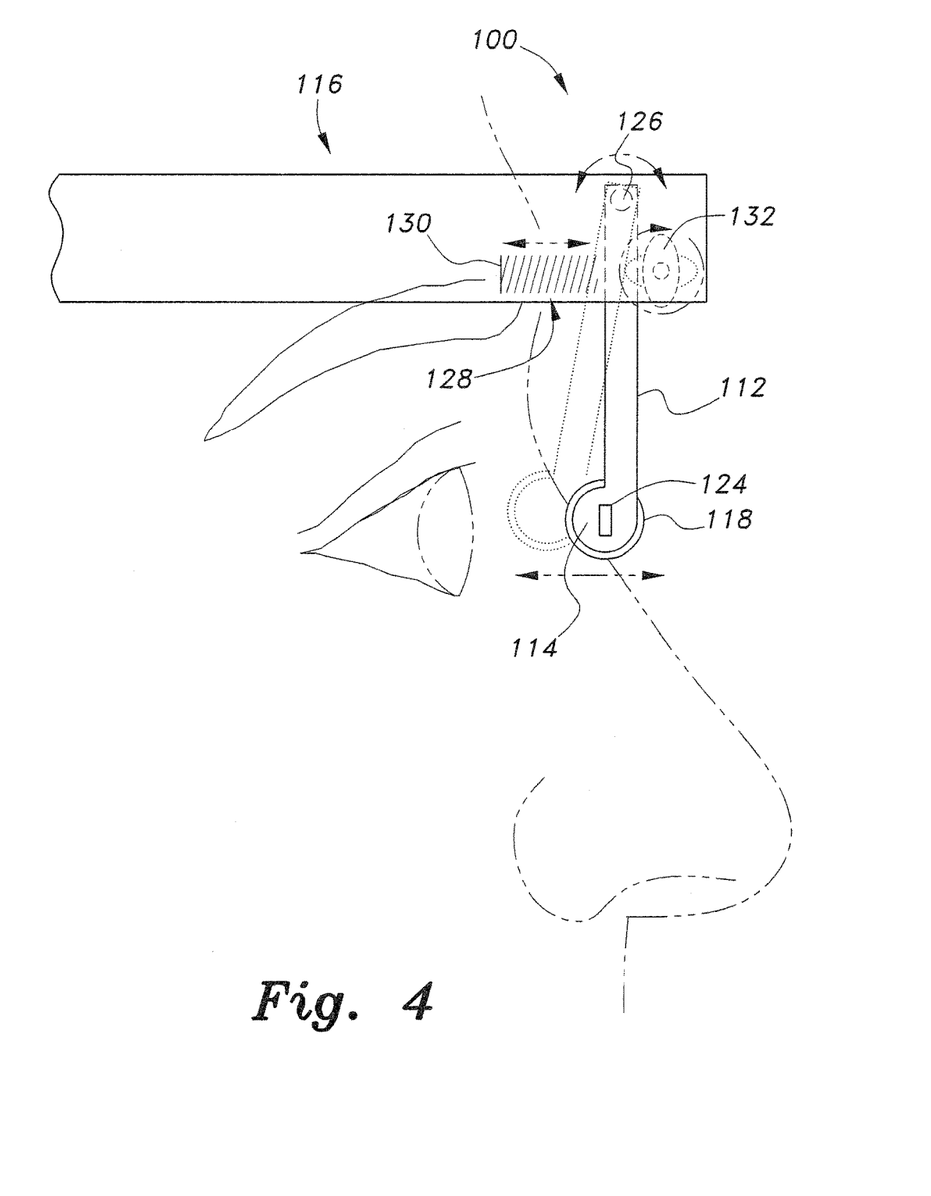
FIG. 4 is an environmental side view of the lacrimal duct therapy device of FIG. 1.
Figure 5:
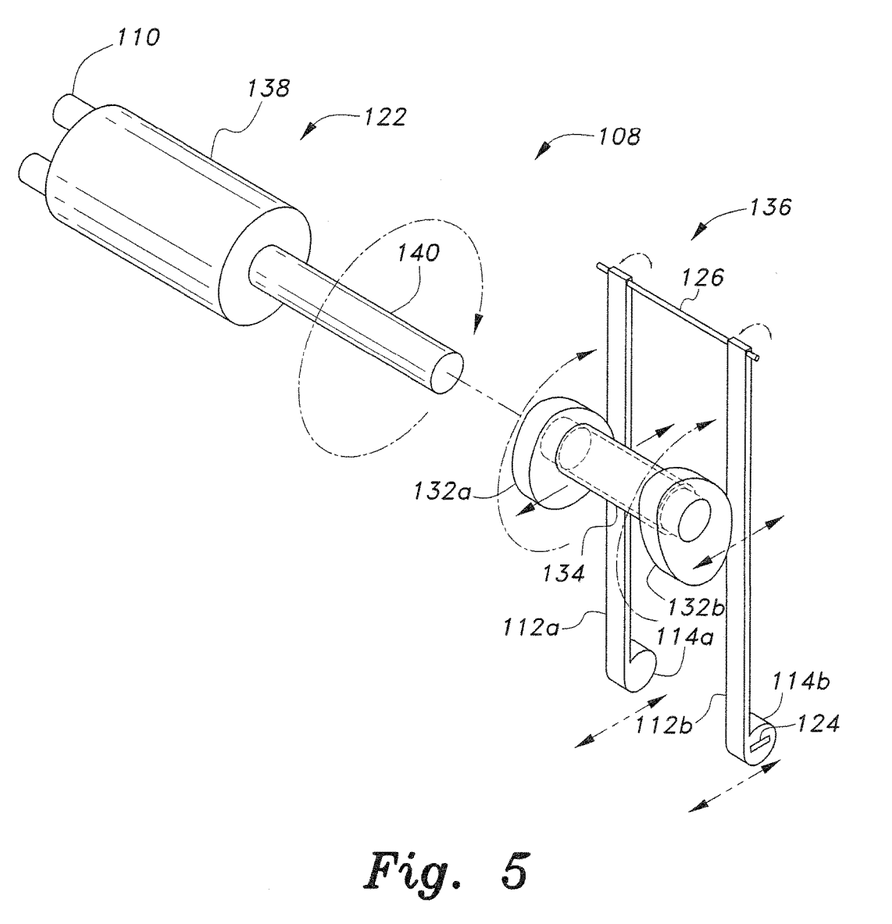
FIG. 5 is an exploded view of an actuator assembly of a lacrimal duct therapy device according to the present invention.

FIG. 4 illustrates the lacrimal duct therapy device attached to the user's head. As shown in FIGS. 4 and 5, the actuator assembly 108 includes a motor assembly 122, which is powered by the power source 110, and a contact assembly 136, which is configured to provide massaging and/or vibrational pressure to selected exterior regions on the user's face proximate to a region exterior to the lacrimal duct. Massaging pressure applied to the exterior region of the lacrimal duct on the face has a therapeutic effect on the lacrimal duct.

The motor assembly 122 includes a motor 138 and a shaft member 140 extending from the motor 138. The shaft member 140 is rotated when the motor 138 is activated by the user. Activation of the motor assembly 122 may be achieved remotely using wireless methods generally known, or by depression of a manual switch.

The contact assembly 136 includes a rod member 134 and dual cam members 132a, 132b disposed on opposing ends of the rod member 134. The rod member 134 is operatively connected to the shaft member 140 of the motor assembly 142, such that rotational movement of the actuator assembly 108 in a selected direction forces the shaft member 140 to rotate in the same direction. The rod member 134 may be hollow and fixed over the free end of the motor shaft 140. The cam members 132a, 132b are rigidly attached to the rod member 134 for rotation therewith.

The contact assembly 136 further includes dual leg members 112a, 112b, which are provided at opposing ends of a pivot pin 126, which supports an end portion of the leg members 112a, 112b. The dual leg members 112a, 112b each have a generally elongated shape, extending in a generally downward direction from the pivot pin 126 for engagement with a region on the user's face proximate to the lacrimal duct. At the end of each respective leg member 112a, 112b is a head or knob member 114a, 114b having a rounded or a partially circular configuration. Each leg member 112a, 112b has a planar first surface positioned for operative engagement with the cam members 132a, 132b and an opposing second surface having a knob member 114a, 114b protruding therefrom to engage the surface of the user's face.

The cam members 132a, 132b may have a conventional lobe shape, so that rotational movement of the cam member 132a, 132b periodically applies a displacing force on the surface of the respective leg members 112a, 112b. As shown, the cam members 132a, 132b each have a generally circular base portion and a lobe portion that extends generally outward from the base portion, forming an oblong shape. The respective lobe portions of the cam members 132a, 132b are configured to apply a force that pushes or displaces the respective leg members 112a, 112b in a protracted outward direction. Movement of the leg members 112a, 112b is controlled according to which portion (lobe portion or base portion) of the cam member 132a, 132b is engaging the respective leg member 112a, 112b. Thus, rotational movement of the cam member 132 dictates whether the leg member 112a or 112b protracts so that the knob 114a or 114b engages or massages the user's face, or retracts, so that the knob 114a or 114b disengages from the user's face.

As the leg member 112a or 112b protracts, it pivots about the axis of the pivot pin 126, extending outward towards the user's lacrimal region, exerting a force on the facial region of the users face proximate to the lacrimal duct region. Repeated engagement of the lacrimal duct region by the respective knobs 114a, 114b provides a therapeutic effect to the user.

Figure 6A:
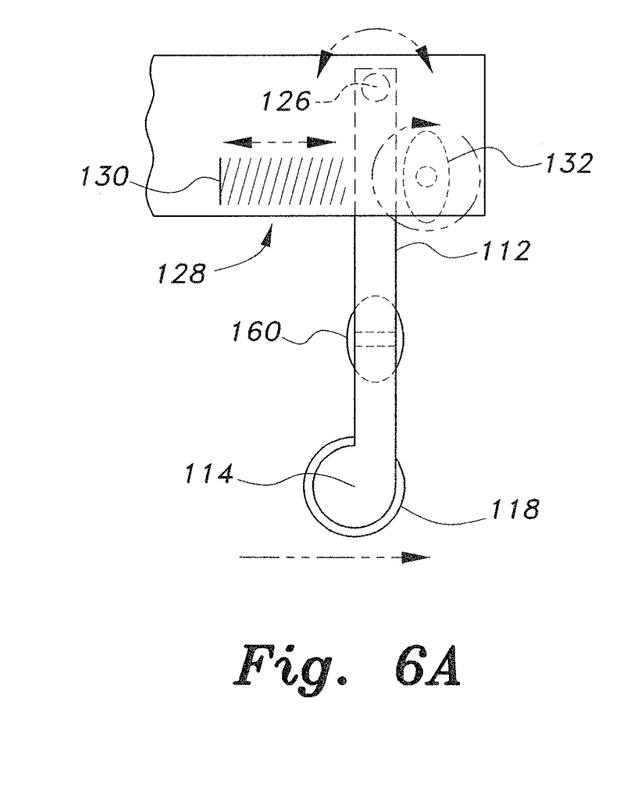
FIG. 6A is a partial side view of a lacrimal duct therapy device according to the present invention, showing the device in a retracted, non-engaging position.
Figure 6B:
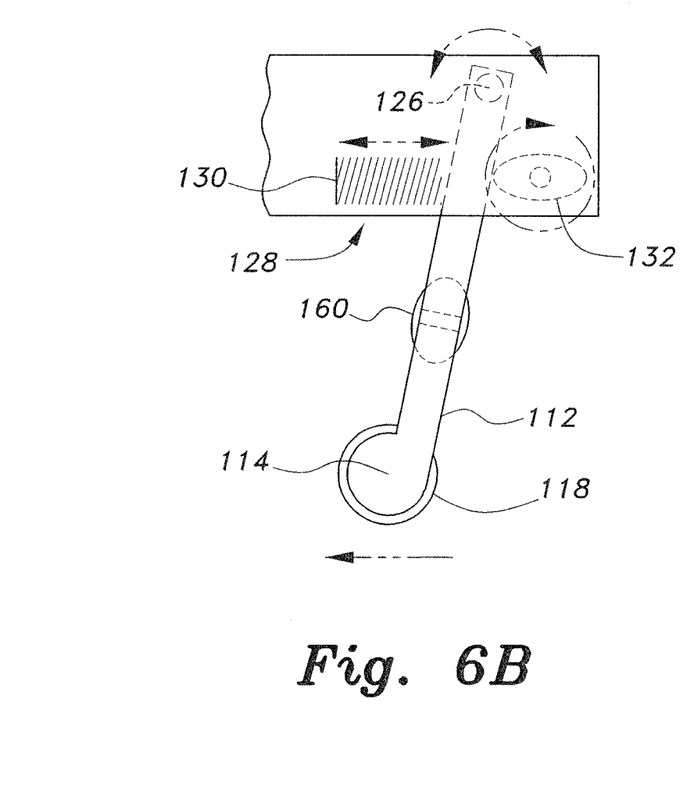
FIG. 6B is a partial side view of a lacrimal duct therapy device according to the present invention, showing the device in a protracted engaging position.

As illustrated in FIG. 4, a biasing member 128 or spring may be positioned to engage each of the respective leg members 112a, 112b opposite side the cam members 132a, 132b, thereby providing a resilient force to assist retracting movement of the respective leg members 112a, 112b when moving from a protracted position to a retracted position. The spring 128 is anchored at a stop member 130. FIG. 6A shows the spring 128 in its extended position with the corresponding leg member 112 oriented vertically, and FIG. 6B shows the spring 128 compressed when the cam 132 rotates to extend the leg member 112 to a protracted position.

The cam members 132a, 132b may be positioned with lobe portions in an aligned configuration so that the leg members 112a, 112b simultaneously apply an engaging force to the user's facial region. Alternatively, as shown in FIG. 5, the lobe portions of the cam members 132a, 132b may be offset from each other radially so that the leg members 112a, 112b exert an alternating force on the user's facial region.

Figure 2:
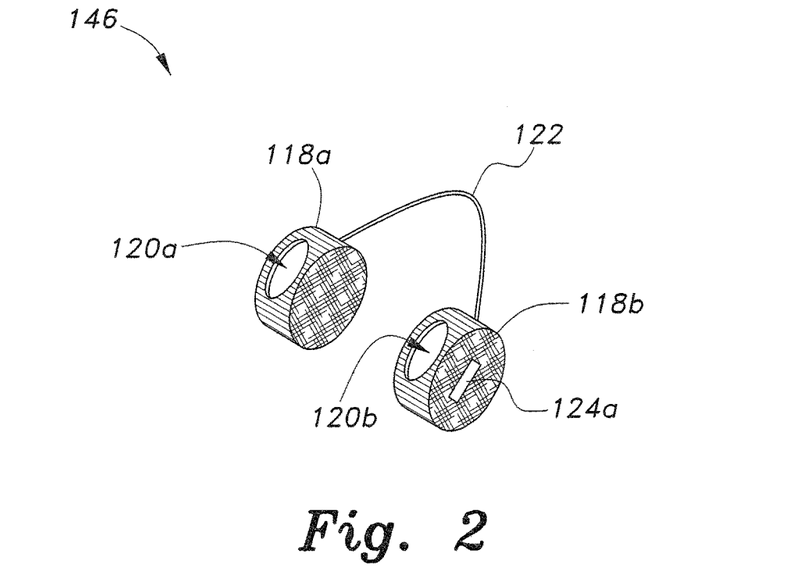
FIG. 2 is a perspective view of dual knob covers for covering engagement portions of the lacrimal duct therapy device according to the present invention.

FIG. 2 shows a cover assembly 146 including dual covers 118a, 118b for optionally covering and cushioning the knob members 114a, 114b. The covers 118a, 118b each have a generally circular configuration, may be connected with a tether 122, and have openings 120a, 120b, which are configured to receive the knob members 114a, 114b therein.

Figure 7A:
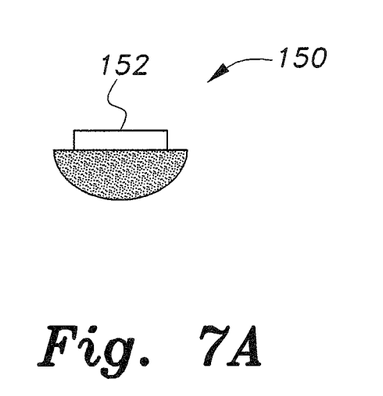
FIG. 7A is a side view of a thermoheating device attachable to a lacrimal duct therapy device according to the present invention.
Figure 7B:
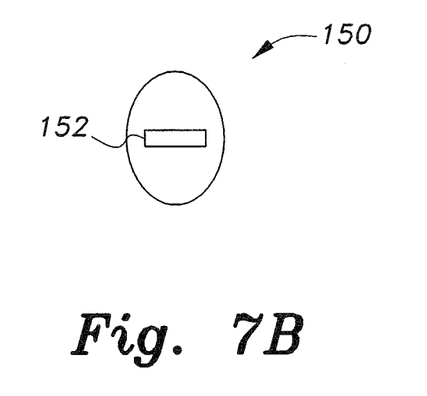
FIG. 7B is a rear view of the thermoheating device of FIG. 7A.
Figure 8:
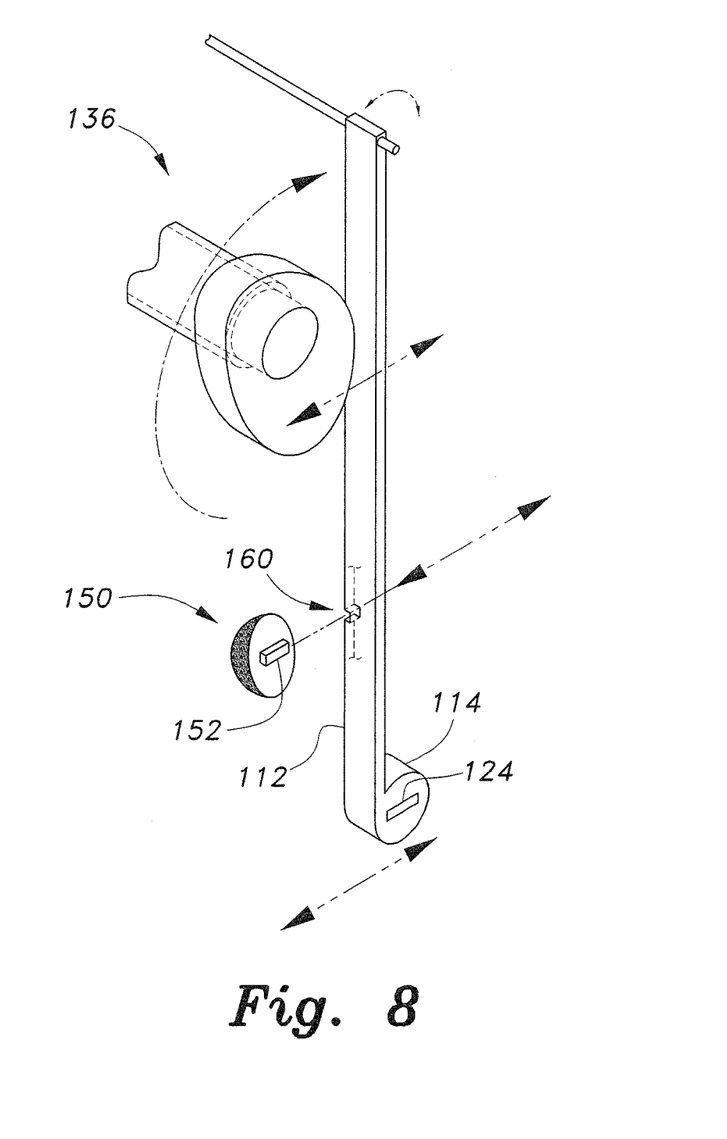
FIG. 8 is a partial side view of a lacrimal duct therapy device according to the present invention, showing the thermoheating device of FIG. 7A exploded from a leg member.

As illustrated in FIGS. 7A, 7B, and 8, a thermoheating device 150 is connectable to the knob members 114 or directly to the leg members 112a, 112b to provide therapeutic heat to the user's face when engaged with the leg member 112 and knob member 114. The thermoheating device 150 includes a tongue 152, which is configured to snap into a groove 160 in the leg member 112, or into a groove 124 on the knob member 114. The covers 118a, 118b may have an opening 124a defined therein through which the tongue 152 may extend, as shown in cover 118b in FIG. 2.

In operation, the user places the lacrimal duct therapy device 100 on his head with the leg members 112a, 112b and knob members 114a, 114b engaged with a region on the face proximate to the lacrimal duct region. The user activates the motor assembly 122, either using a switch or remotely using a wireless device. Once the motor assembly 142 is activated, the motor 138 rotates the shaft member 140, and consequently the rod member 134. The cam members 132a, 132b rotate, applying a protracting displacement force on the leg members 112a, 112b, forcing the leg members 112a, 112b and respective knob members 114a, 114b into massaging therapeutic engagement with the lacrimal duct region on the user's face. Rotation of the cam members 132a, 132b alternately protracts the leg member 112a, 112b into engagement with the face and retracts the leg member 112a, 112b from engagement with the face. This process is repeated, providing therapy to the user's lacrimal duct.

It is to be understood that the present invention is not limited to the embodiments described above, but encompasses any and all embodiments within the scope of the following claims.

I claim:

1. A lacrimal duct therapy device, comprising:
a frame assembly adapted for wearing on a user's head in proximity to bilateral lacrimal duct regions; and
an actuator assembly mounted on the frame assembly, the actuator assembly including:
a motor assembly having a motor and a rotatable shaft extending from the motor; and
a contact assembly having:
an elongated rod member fixed to the motor shaft;
at least one elongated leg member pivotally attached to the frame assembly, the at least one leg member having a free end and a knob protruding from the free end, the knob being adapted for bearing against the user's face over the lacrimal duct region; and
at least one cam member attached to one of the ends of the rod member, the at least one cam member bearing against the at least one leg member, the cam member having a lobe member periodically pivoting the at least one leg member between a protracted position in which the knob applies pressure to the lacrimal duct region and a retracted position in which the pressure is relieved when the motor is actuated in order to massage the lacrimal duct.

2. The lacrimal duct therapy device of claim 1, wherein the frame assembly includes a first arm member, a second arm member, and a bridge member extending between the first and second arm members, the arm members being adapted for being supported on the user's ears with the bridge extending across the user's forehead.

3. The lacrimal duct therapy device of claim 1, further including a spring bearing against the at least one leg member opposite said at least one cam member, the spring being compressed when said at least one cam member pivots the at least one leg member to the protracted position and extending when the lobe no longer pivots the at least one leg member in order to apply spring bias to return the at least one leg member to the retracted position.

4. The lacrimal duct therapy device of claim 1, wherein said at least one leg member comprises a first leg member and a second leg member.

5. The lacrimal duct therapy device of claim 4, wherein at least one cam member comprises a first cam member bearing against the first leg member and a second cam member bearing against the second leg member, the lobes of the first and second cam members being aligned to pivot the first leg member and the second leg member simultaneously.

6. The lacrimal duct therapy device of claim 4, wherein at least one cam member comprises a first cam member bearing against the first leg member and a second cam member bearing against the second leg member, the lobes of the first and second cam members being offset from each other to pivot the first leg member and the second leg member alternately.

7. The lacrimal duct therapy device of claim 1, further comprising a cover assembly removably disposed over the knob of said at least one leg member for cushioning the knob.

8. The lacrimal duct therapy device of claim 1, further comprising a heating device attachable to said knob.

9. The lacrimal duct therapy device of claim 1, further comprising a heating device attachable to said at least one leg member.

10. A lacrimal duct therapy device, comprising:
a frame assembly adapted for wearing on a user's head in proximity to bilateral lacrimal duct regions; and
an actuator assembly mounted on the frame assembly, the actuator assembly including:
a motor assembly having a motor and a rotatable shaft extending from the motor; and
a contact assembly having:
an elongated rod member fixed to the motor shaft, the rod member having opposing ends;
a first elongated leg member and a second elongated leg member pivotally attached to the frame assembly, each of the leg members having a free end and a knob protruding from the free end, the knobs being adapted for bearing against the user's face bilaterally over the lacrimal duct regions; and
first and second cam members attached to the opposing ends of the rod member, respectively, the first can member bearing against the first leg member and the second cam member bearing against the second leg member, each of the cam members having a lobe member periodically pivoting the leg members between a protracted position in which the knob applies pressure to the lacrimal duct region and a retracted position in which the pressure is relieved when the motor is actuated in order to massage the lacrimal ducts bilaterally.

11. The lacrimal duct therapy device according to claim 10, wherein the frame assembly includes a first arm member, a second arm member, and a bridge member extending between the first and second arm members, the arm members being adapted for being supported on the user's ears with the bridge extending across the user's forehead.

12. The lacrimal duct therapy device according to claim 10, further including a first spring bearing against the first leg member opposite said first cam member and a second spring bearing against the second leg member opposite said second cam member, the springs being compressed when said the corresponding cam member pivots the corresponding leg member to the protracted position and extending when the lobe no longer pivots the corresponding leg member in order to apply spring bias to return the corresponding leg member to the retracted position.

13. The lacrimal duct therapy device according to claim 10, wherein the lobes of the first and second cam members are aligned to pivot the first leg member and the second leg member simultaneously.

14. The lacrimal duct therapy device according to claim 10, wherein the lobes of the first and second cam members are offset from each other to pivot the first leg member and the second leg member alternately.

15. The lacrimal duct therapy device according to claim 10, further comprising a cover assembly removably disposed over the knobs of said leg members for cushioning the knobs.

16. The lacrimal duct therapy device according to claim 10, further comprising a heating device attachable to said knobs.

17. The lacrimal duct therapy device according to claim 1, further comprising a heating device attachable to said leg members.

* * * * *